United States Patent
Chono

(10) Patent No.: US 9,572,547 B2
(45) Date of Patent: Feb. 21, 2017

(54) ULTRASONIC DIAGNOSIS APPARATUS AND METHOD FOR PRESENTING ITEMS FOR INSPECTION

(75) Inventor: Tomoaki Chono, Tokyo (JP)

(73) Assignee: HITACHI, LTD., Tokyo (JP)

(*) Notice: Subject to any disclaimer, the term of this patent is extended or adjusted under 35 U.S.C. 154(b) by 421 days.

(21) Appl. No.: 14/117,447

(22) PCT Filed: May 16, 2012

(86) PCT No.: PCT/JP2012/062460
§ 371 (c)(1),
(2), (4) Date: Nov. 13, 2013

(87) PCT Pub. No.: WO2012/161040
PCT Pub. Date: Nov. 29, 2012

(65) Prior Publication Data
US 2014/0309530 A1 Oct. 16, 2014

(30) Foreign Application Priority Data
May 23, 2011 (JP) .................................. 2011-114288

(51) Int. Cl.
*A61B 8/00* (2006.01)
*A61B 8/08* (2006.01)
*G06F 19/00* (2011.01)

(52) U.S. Cl.
CPC .................. *A61B 8/469* (2013.01); *A61B 8/00* (2013.01); *A61B 8/463* (2013.01); *A61B 8/467* (2013.01);
(Continued)

(58) Field of Classification Search
CPC ....... A61B 8/463; A61B 8/469; A61B 8/5223; A61B 8/585; A61B 8/467; A61B 8/00; A61B 8/0883; A61B 8/08; G06F 19/3406
See application file for complete search history.

(56) References Cited

U.S. PATENT DOCUMENTS

| 6,458,081 B1 | 10/2002 | Matsui et al. |
| 7,551,755 B1 * | 6/2009 | Steinberg ........... G06K 9/00228 340/5.53 |

(Continued)

FOREIGN PATENT DOCUMENTS

| JP | A-3-261459 | 11/1991 |
| JP | A-10-305034 | 11/1998 |

(Continued)

OTHER PUBLICATIONS

International Search Report issued in International Patent Application No. PCT/JP2012/062460 dated Aug. 21, 2012.
(Continued)

*Primary Examiner* — Bo J Peng
(74) *Attorney, Agent, or Firm* — Oliff PLC

(57) ABSTRACT

An ultrasonic diagnosis apparatus according to the present invention includes: a storing section storing a plurality of items for inspection including ultrasonic imaging or measurement of an imaged ultrasonogram and an order thereof; a controlling section calculating, regarding an item set for inspection constituted of a next item for inspection which is an item for inspection subsequent to a current item for inspection which is currently being implemented out of the plurality of items for inspection, an implementation frequency at which the item set for inspection is implemented, for each next item for inspection; a displaying section displaying a candidate for the next item for inspection on the basis of the implementation frequency; and an inputting section inputting the next item for inspection from the candidate for the next item for inspection.

11 Claims, 14 Drawing Sheets

(52) U.S. Cl.
CPC .............. *A61B 8/5223* (2013.01); *A61B 8/585* (2013.01); *A61B 8/08* (2013.01); *A61B 8/0883* (2013.01); *G06F 19/345* (2013.01); *G06F 19/3406* (2013.01)

(56) References Cited

U.S. PATENT DOCUMENTS

2007/0022377 A1   1/2007  Haider et al.
2008/0075321 A1   3/2008  Kabasawa

FOREIGN PATENT DOCUMENTS

| | | |
|---|---|---|
| JP | A-2001-137237 | 5/2001 |
| JP | A-2001-299749 | 10/2001 |
| JP | A-2005-168542 | 6/2005 |
| JP | A-2008-73228 | 4/2008 |
| JP | A-2009-77960 | 4/2009 |

OTHER PUBLICATIONS

Oct. 14, 2015 Office Action issued in Chinese Patent Application No. 201280024885.8.

\* cited by examiner

| KIND \ ORDER | 1 | 2 | 3 |
|---|---|---|---|
| HEART INSPECTION 1 | EF | PW | TDI |
| HEART INSPECTION 2 | LV | PW | CW |
| HEART INSPECTION 3 | EF | CFM | LV |
| ⋮ | ⋮ | ⋮ | ⋮ |

ULTRASONIC DIAGNOSIS APPARATUS AND METHOD FOR PRESENTING ITEMS FOR INSPECTION

TECHNICAL FIELD

The present invention relates to an ultrasonic diagnosis apparatus and a method for presenting items for inspection in the same for presenting, to the inspector, a plurality of candidates for an item for inspection (referred to as next item for inspection) next to an item for inspection currently being implemented (referred to as current item for inspection).

BACKGROUND ART

In an ultrasonic diagnosis apparatus, a plurality of kinds of items for inspection are performed as routine inspection for each medical department or each disease, the plurality of kinds of items for inspection being done in specific orders, and constitute a plurality of kinds of sets of items for inspection performed in these orders (referred to as item sets for inspection). Regarding the item sets for inspection, Patent Literature 1 discloses the following steps.

Step 1: step of accumulating usage counts of the past item sets for inspection

Step 2: step of registering, when the accumulated usage count of an item set for inspection reaches a defined number, it as an "item set for inspection whose usage count reaches the defined number"

Step 3: step of selecting a standard item set for inspection out of the registered "item sets for inspection whose usage counts reach the defined number"

Step 4: step of registering the selected item set for inspection in a recording section

CITATION LIST

Patent Literature

Patent Literature 1: JP-A-2009-77960

SUMMARY OF INVENTION

Technical Problem

In Patent Literature 1, since one item set for inspection which is registered in the recording section is provided, it is considered that a view point of improvement of operability when an item for inspection different from the next item for inspection registered in the relevant item set for inspection is wanted to be implemented after implementing the current item for inspection has not been investigated.

Therefore, an object of the present invention is to provide an ultrasonic diagnosis apparatus and a method for presenting items for inspection in the same capable of improving operability in selecting a next item for inspection after a current item for inspection in an item set for inspection.

Solution to Problem

To achieve the above-mentioned object, the present invention stores a plurality of items for inspection including ultrasonic imaging or measurement of an imaged ultrasonogram and an order thereof, calculates, regarding an item set for inspection constituted of a current item for inspection which is currently being implemented and a next item for inspection which is an item for inspection subsequent to the relevant current item for inspection out of the plurality of items for inspection, an implementation frequency at which the item set for inspection is implemented, for each next item for inspection, displays a candidate for the next item for inspection on the basis of the implementation frequency, and inputs the next item for inspection from the candidate for the next item for inspection.

Advantageous Effects of Invention

According to the present invention, operability in selecting a next item for inspection after a current item for inspection in an item set for inspection can be improved.

DESCRIPTION OF EMBODIMENTS

Embodiments for implementing the invention are described as follows.

Embodiment 1

Figure 1:
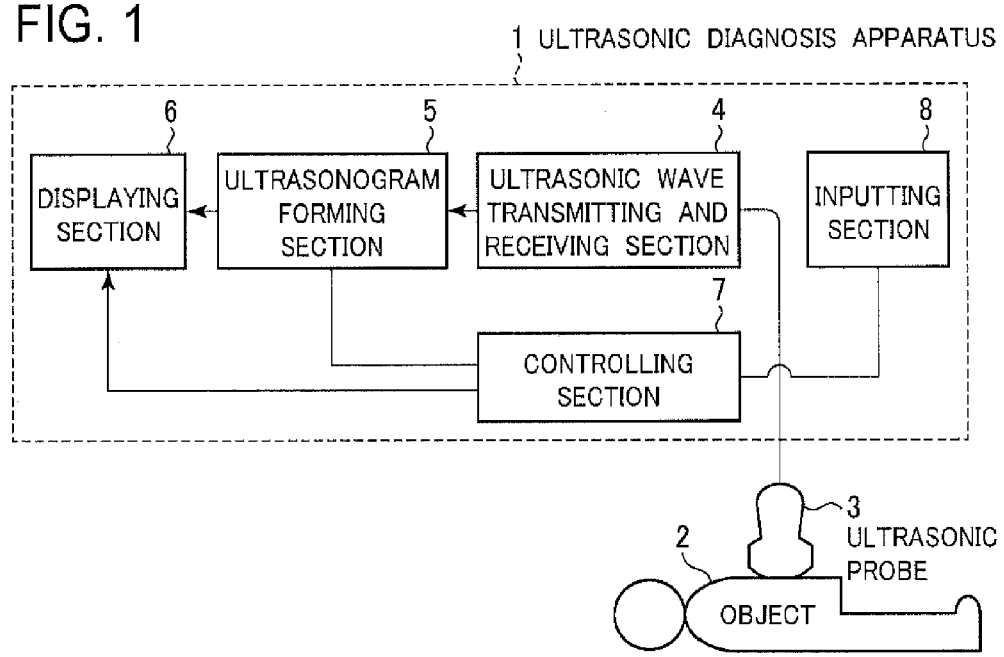
FIG. 1 is a block diagram showing an exemplary configuration of an ultrasonic diagnosis apparatus to which the present invention is applied.

In Embodiment 1, a method for presenting candidates for a next item for inspection using a Markov model is described. An ultrasonic diagnosis apparatus adopted in Embodiment 1 is described in detail using figures. FIG. 1 is a block diagram showing a configuration of an ultrasonic diagnosis apparatus to which the present invention is applied.

An ultrasonic diagnosis apparatus 1 shown in FIG. 1 is one which configures and displays a two-dimensional ultrasonogram, a three-dimensional ultrasonogram or various kinds of Doppler images of a diagnosis portion using an echo signal obtained by transmitting and receiving an ultrasonic wave into a object 2, and includes constituents of an ultrasonic probe 3, an ultrasonic wave transmitting and receiving section 4, an ultrasonogram forming section 5, a displaying section 6, a controlling section 7 and an inputting section 8.

The ultrasonic probe 3 is one which receives a reflected echo after transmitting an ultrasonic wave to the object 2, and is constituted of a plurality of oscillation elements which are arranged for 1 to m channels in a longitudinal axis direction. The ultrasonic wave transmitting and receiving section 4 is one which generates a pulse-like electric signal for generating an ultrasonic signal transmitted to the object 2 and transmits this to the ultrasonic probe 3, and in addition, which performs signal processing on an electric signal obtained by converting the echo signal received by the ultrasonic probe 3. The ultrasonogram forming section 5 is one which forms various kinds of ultrasonograms including a two-dimensional ultrasonogram, a three-dimensional ultrasonogram or a Doppler image from the electric signal having undergone the signal processing. The displaying section 6 is one which displays the ultrasonogram formed by the ultrasonogram forming section 5. The controlling section 7 is one which controls the individual elements of the ultrasonic wave transmitting and receiving section 4, the ultrasonogram forming section 5 and the displaying section 6. The inputting section 8 is one which gives, to the controlling section 7, inputted instructions, the inspector inputting the instructions to the individual elements via an inputting device such as a keyboard and a pointing device attached to the inputting section 8 itself.

Figure 2:
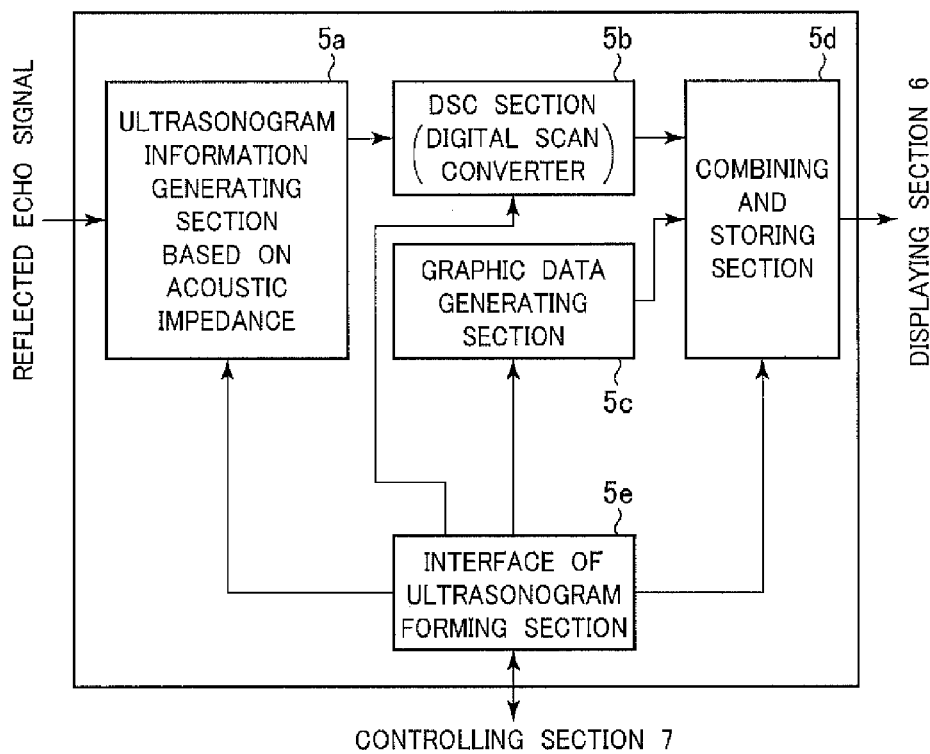
FIG. 2 is a block diagram showing an exemplary configuration of an ultrasonogram forming section 5 in FIG. 1.

FIG. 2 is a block diagram showing an exemplary configuration of the ultrasonogram forming section 5 in FIG. 1.

The ultrasonogram forming section 5 shown in FIG. 2 includes constituents of an ultrasonogram information generating section 5a, a digital scan converter section (referred to as DSC section; Digital Scan Converter) 5b, a graphic data generating section 5c, a combining and storing section 5d and an interface 5e.

The ultrasonogram information generating section 5a is one which generates ultrasonogram information of the inspection object using the echo signal undergoing the signal processing. The DSC section 5b is one which scans and converts the ultrasonogram information generated by the ultrasonogram information generating section 5a into a television display image pattern to generate ultrasonogram data. The graphic data generating section 5c is one which generates graphic data such as scales, marks and characters to be attached to an image which is based on image data obtained by the scanning and conversion of the DSC section 5b. The combining and storing section 5d is one which combines and stores the ultrasonogram data generated by the DSC section 5b and the graphic data generated by the graphic data generating section 5c, and has a hard disk, a temporary storage memory RAM and the like. The interface 5e is an interface of the ultrasonogram forming section 5 for reading out, from the controlling section 7 under the control of the controlling section 7, initial values, control parameters and the like required for various kinds of processing of the ultrasonogram information generating section 5a which generates the ultrasonogram information, the DSC section 5b, the graphic data generating section 5c and the combining and storing section 5d to configure them to the ultrasonogram information generating section 5a, the DSC section 5b, the graphic data generating section 5c and the combining and storing section 5d.

Figures 3, 4:
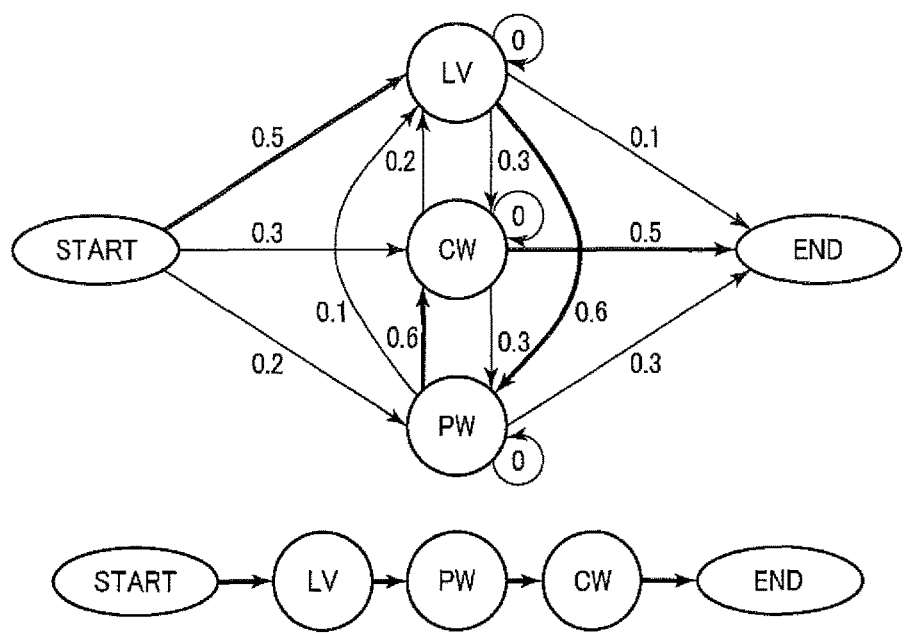
FIG. 3 is a diagram for explaining of a function of database of item sets for inspection in a combining and storing section 5d in FIG. 2.
FIG. 4 is a diagram for explaining a calculation function of implementation probabilities of items for inspection according to Embodiment 1 using a Markov model.

FIG. 3 is a diagram for explaining a database function of item sets for inspection in the combining and storing section 5d of FIG. 2.

The combining and storing section 5d is also a storing section of item sets for inspection, functioning as a database of the item sets for inspection. In the database of item sets for inspection, item sets for inspection which underwent inspection and implementation in the past are stored. The item sets for inspection are registered in a database of item sets for inspection in association with medical departments and genders and disease information of the objects 2. Herein, routine inspection in a cardiovascular department is presented as an example. In the combining and storing section 5d, a table 31 shown in FIG. 3 is stored. The table 31 presents two axes for which items in the vertical direction are defined as kinds of inspection (simplified as a kind in FIG. 3) and items in the horizontal direction as orders of items for inspection (simplified as an order in FIG. 3). The kind employs "heart inspection 1", "heart inspection 2" and "heart inspection 3", and the order indicates that items for inspection are implemented in ascending order of the numbers. The items for inspection are represented by alphabetical abbreviations with two characters or three characters. Meanings of the alphabetical abbreviations are as follows. "EF" means measurement of a cardiac ejection fraction of the heart of the object. "PW" means imaging the heart of the object using a pulse Doppler method. "TDI" is an abbreviation of Tissue Doppler Imaging and means, for example, analyzing a myocardium length change of the heart of the object 2 to measure a left ventricular wall thickness change and the like. "LV" means imaging an ultrasonogram of the left ventricle of the object and measuring an LVDd (Left Ventricular end Diastolic internal diameter). "CW" means imaging the heart of the object using a continuous wave Doppler method. "CFM" means imaging the heart of the object as a color flow mapping image.

Thus, in the table 31, "EF" to "PW" to "TDI" in "heart inspection 1", "LV" to "PW" to "CW" in "heart inspection 2", and "EF" to "CFM" to "PV" in "heart inspection 3" are stored as item sets for inspection for cardiac surgery. The inspector inputs that the inspector implements "heart inspection 2" using the inputting device prepared in the inputting section 8.

The displaying section 6 displays the table 31 when selecting implementation of "heart inspection 2".

The displaying section 6 is one which displays the image formed by the ultrasonogram forming section 5 as an ultrasonogram, and includes, for example, a CRT monitor, a liquid crystal monitor or the like.

The controlling section 7 is one which controls operation of the individual constituents under the instructions from a console 8, and is configured of a computer system for control which has an interface to a user interface circuit. Specifically, the controlling section 7 controls the ultrasonic wave transmitting and receiving section 4 and the ultrasonogram forming section 5 from the interface included in the controlling section 7 and on the basis of information and the like from the interface. Moreover, it performs control of transmitting information obtained by conversion into an image in the ultrasonogram forming section 5 to the displaying section 6 and the like.

FIG. 4 is a diagram for explaining a calculation function of implementation probabilities of items for inspection according to Embodiment 1 using a Markov model.

The controlling section 7 has, as described below, a calculation function of implementation probabilities of items for inspection by which an implementation probability of a next item for inspection with respect to a current item for inspection is calculated for each item for inspection in an item set for inspection for the past item sets for inspection stored in the database of item sets for inspection in the combining and storing section 5d.

A calculation function of implementation probabilities of items for inspection shown in FIG. 4 is described using an example of transition of "inspection start" to "LV" to "PW" to "CW" to "inspection end" in "heart inspection 2".

First, in "inspection start", for a next item for inspection (first time item for inspection), an implementation probability of "LV" being 0.5, an implementation probability of "PW" being 0.2 and an implementation probability of "CW" being 0.3 are stored along with the past item sets for inspection in the combining and storing section 5d. Herein, as indicated by a bold arrow in the figure, "LV" is selected as "first time item for inspection", and the implementation probability of "LV" being 0.5 is a conditional probability by which the next item for inspection (first time item for inspection) is multiplied.

Next, in "first time item for inspection", for a second time item for inspection, an implementation probability of "LV" being 0×0.5, an implementation probability of "PW" being 0.6×0.5 and an implementation probability of "CW" being 0.3×0.5 are stored along with the past item sets for inspection in the combining and storing section 5d. Herein, as indicated by a bold arrow in the figure, "PW" is selected as "second time item for inspection", and the implementation probability of "PW" being 0.6×0.5 is a conditional probability by which the next item for inspection (second time item for inspection) is multiplied.

Next, in "second time item for inspection", for a third time item for inspection, an implementation probability of "LV" being 0.1×0.6×0.5, an implementation probability of "PW" being 0 and an implementation probability of "CW" being 0.9×0.6×0.5 are stored along with the past item sets for inspection in the combining and storing section 5d. Herein, as indicated by a bold arrow in the figure, "CW" is selected as "third time item for inspection", and the implementation probability of "CW" being 0.9×0.6×0.5 is a conditional probability by which the next item for inspection (inspection end) is multiplied.

Finally, in "third item for inspection", for an inspection end, an implementation probability of "LV" being 0.2, an implementation probability of "PW" being 0.3, an implementation probability of "CW" being 0 and an implementation probability of "inspection end" being 0.5 are stored along with the past item sets for inspection in the combining and storing section 5d. Herein, as indicated by a bold arrow in the figure, "inspection end" is selected, and an implementation probability 0.5×0.6×0.6×0.5 is an overall probability of processing of "inspection start" to "LV" to "PW" to "CW" to "inspection end" in "heart inspection 2".

The controlling section 7 causes the combining and storing section 5d to store the calculated implementation probabilities of the individual next items for inspection.

Figure 5:
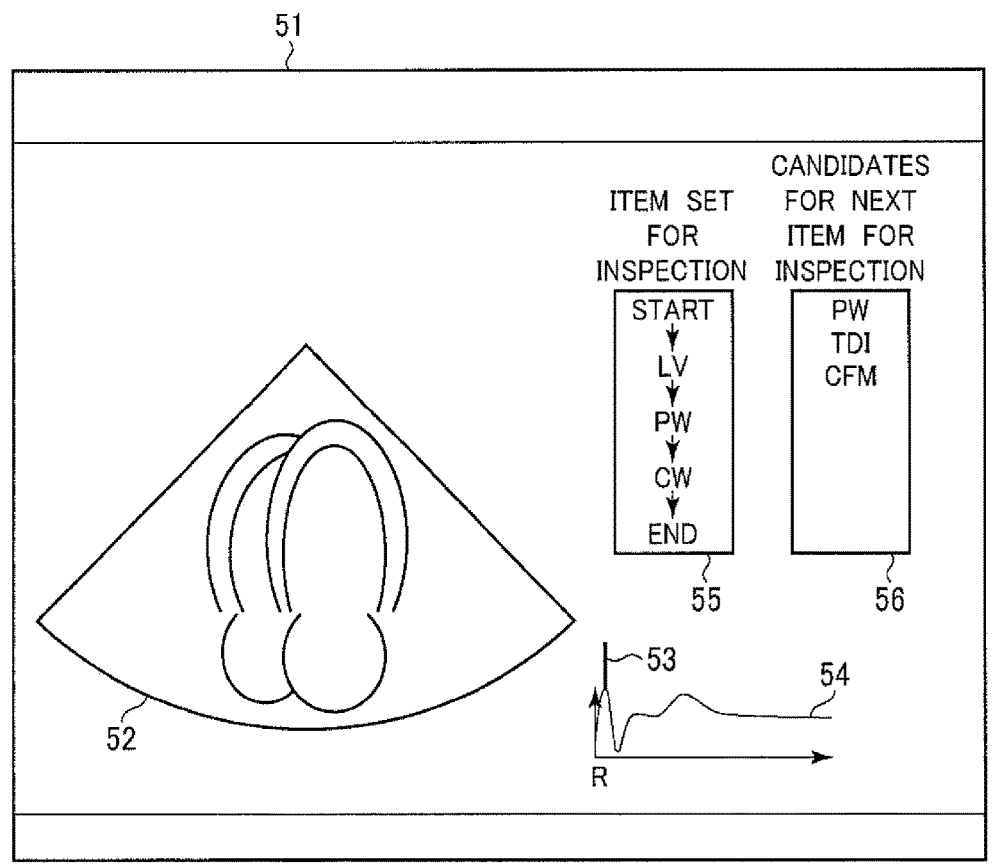
FIG. 5 is a diagram for explaining display of candidates for a next item for inspection in a displaying region 56 of a displaying section 6 in FIG. 1.

FIG. 5 is a diagram for explaining that a next item for inspection is displayed in a displaying region of the displaying section 6 in which the ultrasonogram is not displayed.

The controlling section 7 presents the item set for inspection selected as mentioned above, and furthermore, presents items for inspection for which the implementation probability of a next item for inspection is present as next items for inspection. As a method of the presentation, as described in FIG. 5, in order to prevent overlapping with a region 52 of the displaying section 6 in which the ultrasonogram is displayed, they are displayed, for example, in descending order of probability in a displaying region 55 different from the region 52 in which the ultrasonogram is displayed.

On a screen 51 of the displaying section 6 in FIG. 5, an apical four-chamber view of the heart of the object is displayed in the displaying region 52 of the ultrasonogram. Moreover, in the lower right to the displaying region 52 on the screen 51 of the displaying section 6, an electrocardiogram 54 is displayed and, on the waveform of the electrocardiogram 54, a cardiac time phase bar 53 is displayed which indicates time of obtaining the apical four-chamber view, respectively. Moreover, in the upper right to the displaying region 52 on the screen 51 of the displaying section 6, a displaying region 55 in which an item set for inspection and a displaying region 56 in which next items for inspection are displayed.

Figure 6:
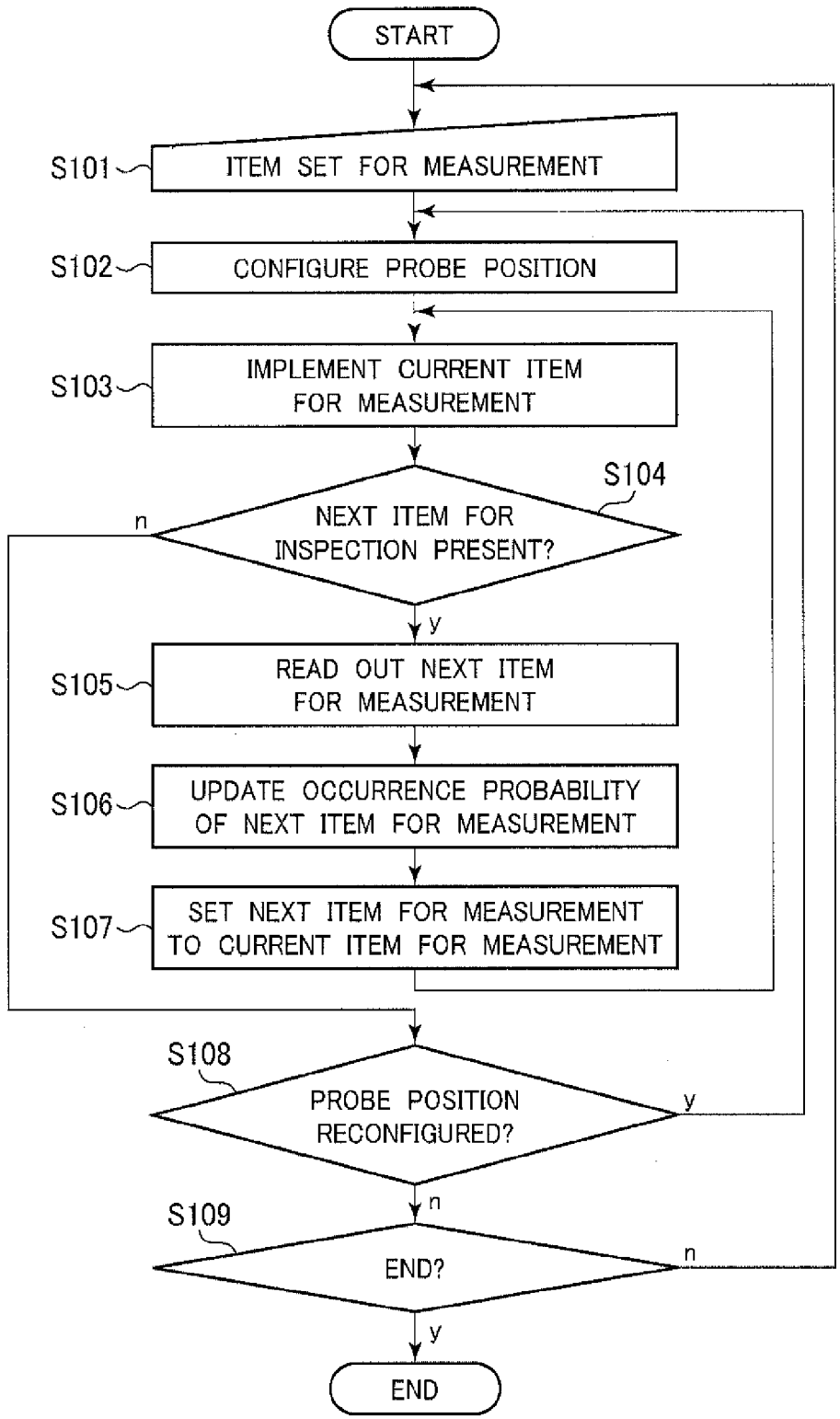
FIG. 6 is a flowchart for explaining an operation example according to Embodiment 1.
Figure 7:
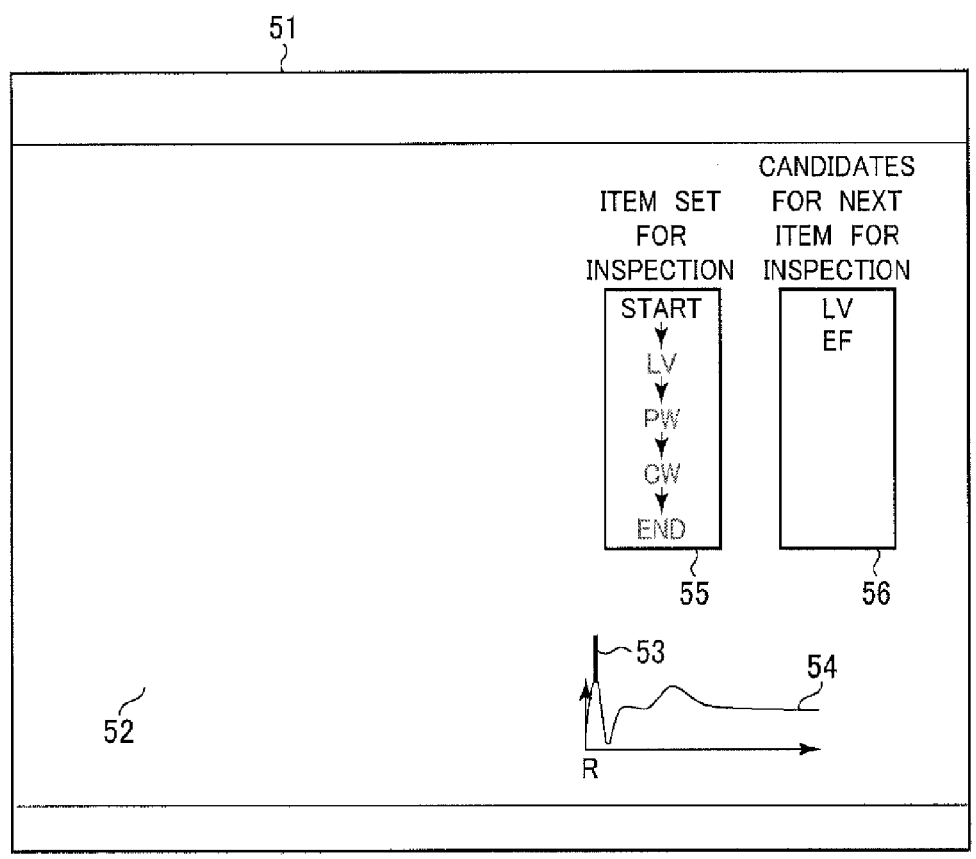
FIG. 7 is a diagram for explaining a display example of the displaying section 6 in "inspection start (START)" which is one process of operation in FIG. 6.

Next, a procedure of implementing "heart inspection 2" out of item sets for inspection is described using FIG. 6 to FIG. 11. FIG. 6 is a flowchart for explaining an operation example according to Embodiment 1. FIG. 7 is a diagram for explaining a display example of the displaying section 6 in "inspection start (START)" which is a process of operation in FIG. 6.

[Step S101]

The controlling section 7 generates an initial screen as shown in FIG. 7, and the initial screen is displayed on the displaying section 6. As to the individual signs in FIG. 7, the portion which is described in FIG. 5 is omitted and a different portion from FIG. 5 is described. In the displaying region 55 of the item set for inspection in FIG. 7, the item for inspection "START" is in the displayed state. Moreover, the items for inspection except the item for inspection "START" are in the non-displayed state in which they are indicated by outlined characters. In addition, the item for inspection in the displayed state only has to be different in displaying mode such as color and blinking display from the individual items for inspection in the non-displayed state. As above, by setting the current item for inspection in the displayed state in which it only be made conspicuous, since the current item for inspection can be clearly discriminated from the next item for inspection, items for inspection which have been already implemented, and the like, the inspector can quickly recognize progress of the item set for inspection.

The inspector inputs the item set for measurement of "heart inspection 2" using the inputting device of the inputting section 8.

[Step S102]

The inspector brings the ultrasonic probe 3 in contact with the chest part of the object 2 and configures a position for measuring the heart of the object 2.

[Step S103: LV]

The controlling section 7 gives, to the ultrasonic wave transmitting and receiving section 4, the ultrasonogram forming section 5 and the displaying section 6, control amounts for measuring the current item for measurement "LV" which is performed upon accepting the input from the inputting device.

Moreover, the controlling section 7 updates the implementation probability of the current item for inspection "inspection start" to the next item for inspection "LV" since the implementation frequency in the current item for inspection "inspection start" to the next item for inspection "LV" increases by one event.

For example, as shown in FIG. 4, the implementation probability of the current item for inspection "inspection start" to the next item for inspection "LV" is 0.5, the implementation probability of the current item for inspection "inspection start" to the next item for inspection "CW" is 0.3, and the implementation probability of the current item for inspection "inspection start" to the next item for inspection "PW" is 0.2.

A probability in which an event is implemented next (implementation probability) and a probability in which not implemented (non-implementation probability) are represented by the following general formulae.

Implementation probability=(the number of the relevant events in the past+1)/(the number of the total events in the past+1)

Non-implementation probability=the number of the relevant events in the past/(the number of the total events in the past+1)

The basis for these probability calculations are described as follows. First, it is supposed that the number of the total events in the past is 10 times and the number of the relevant events in the past is 5 times in the current item for inspection "inspection start" to the next item for inspection "LV", that the number of the relevant events in the past is 3 times in the current item for inspection "inspection start" to the next item for inspection "CW", and that the number of the relevant events in the past is 2 times in the current item for inspection "inspection start" to the next item for inspection "PW". It is supposed that, this time, the number of the total events is 11 times and an event in the current item for inspection "inspection start" to the next item for inspection "LV" arises. The implementation probability (the current item for inspection "inspection start" to the next item for inspection "LV") is updated to 0.54, the non-implementation probabilities to 0.27 (probability for the current item for inspection "inspection start" to the next item for inspection "CW"), and to 0.18 (probability for the current item for inspection "inspection start" to the next item for inspection "PW"), respectively. Moreover, the conditional probability for transfer of "first time item for inspection" to "second time item for inspection" is the implementation probability of the current item for inspection "inspection start" to the next item for inspection "LV" being 0.54.

Figure 8:
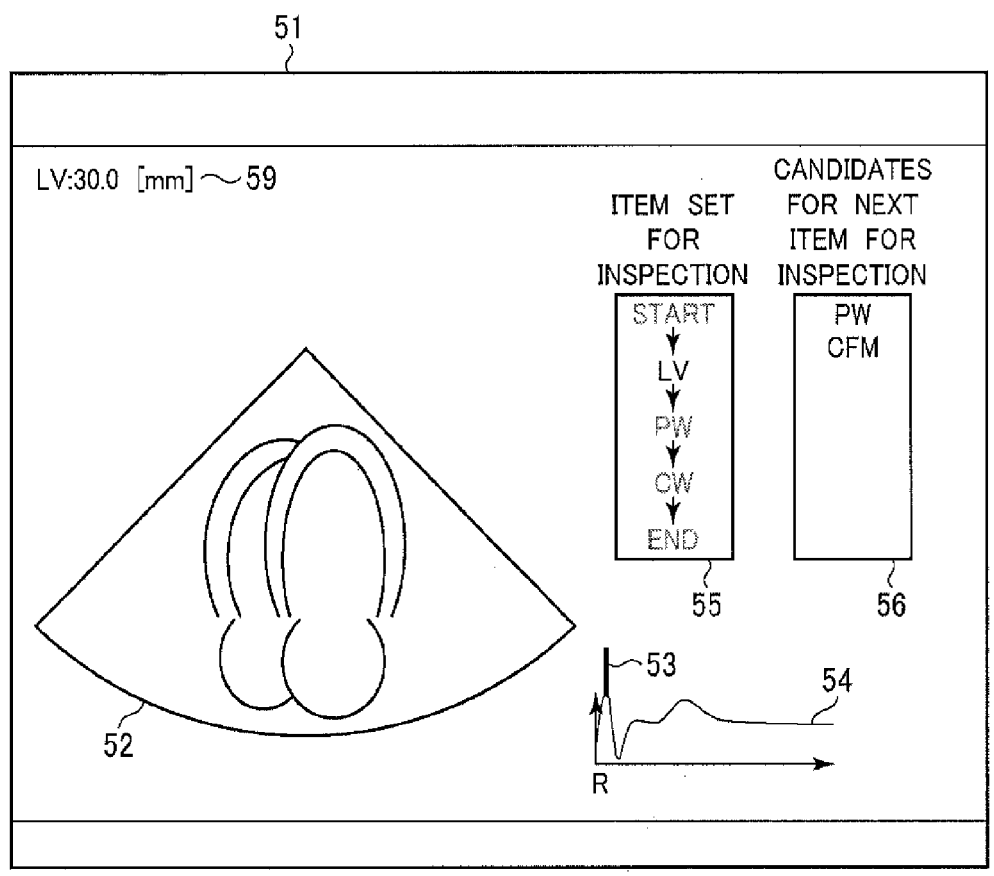
FIG. 8 is a diagram for explaining a display example of the displaying section 6 in "first time item for inspection" which is one process of operation in FIG. 6.

Thereby, the displayed state of the displaying section 6 is moved from FIG. 7 to FIG. 8.

FIG. 8 is a diagram for explaining a display example of the displaying section 6 in "first time item for inspection" which is a process of operation in FIG. 6. As to the individual signs in FIG. 8, the portion which is described in FIG. 5 is omitted and a different portion from FIG. 5 is described. In the displaying region 55 of the item set for inspection in FIG. 8, the current item for inspection LV is in the displayed state and the items for inspection except the current item for inspection LV are in the non-displayed state in which they are indicated by outlined characters, and thereby, the current item for inspection can be discriminated from the other items for inspection, these being displayed.

The ultrasonic probe 3 converts a pulse-like electric signal which is for generating an ultrasonic signal and is transmitted from the ultrasonic wave transmitting and receiving section 4 into an ultrasonic wave to transmit it to the object 2, receives the echo signal reflected from the object 2, converts the received echo signal to an electric signal, and returns it to the ultrasonic wave transmitting and receiving section 4. The ultrasonic wave transmitting and receiving section 4 performs signal processing on the electric signal obtained by the conversion of the echo signal received by the ultrasonic probe 3. The ultrasonogram forming section 5 forms a two-dimensional ultrasonogram from the electric signal having undergone the signal processing. The displaying section 6 displays the ultrasonogram formed by the ultrasonogram forming section 5. As to the left ventricular end diastolic internal diameter of the heart of the object 2, the inspector measures, using the inputting device, the left ventricular internal diameter on the ultrasonogram displayed on the displaying section 6 by means of known distance measurement, referring to the electrocardiogram 54, and the measurement value is displayed in a displaying region 59 of the displaying section 6.

Moreover, in the ultrasonogram, for the left ventricular internal diameter as the measurement object, the region, called lumen, in which blood is filled is separated from the region of the myocardium which covers the lumen region, and difference between the region of the lumen and the region of the myocardium in grayscale of the image is clear. Therefore, the left ventricular internal diameter is always being measured, and the measurement value only at the end diastolic in the electrocardiogram is displayed in the displaying region 59 of the displaying section 6.

As above, the implementation of the current item for measurement "LV" completes.

[Step S104: LV to PW]

The controlling section 7 determines the presence or absence of a next item for inspection. In this case, since the next item for inspection "PW" of the current item for inspection "LV" is present, the controlling section 7 performs branching to the presence of a next item for inspection, that is, "y" and moves to step S105.

[Step S105: PW]

The controlling section 7 reads out the next item for inspection "PW" and the implementation probability of "PW" being 0.6×0.5 from the combining and storing section 5*d*, and displays the next item for inspection "PW" in the displaying region 56.

[Step S106: PW]

Since the implementation frequency in the current item for inspection "LV" to the next item for inspection "PW" increases by one event, the controlling section 7 updates the implementation probability of the current item for inspection "LV" to the next item for inspection "PW".

For example, as shown in FIG. 4, the implementation probability of the current item for inspection "LV" to the next item for inspection "PW" is 0.6, the implementation probability of the current item for inspection "LV" to the next item for inspection "CW" is 0.3, and the implementation probability of the current item for inspection "LV" to the next item for inspection "END" is 0.1. It is supposed that the basis of these probability calculations is in that, out of 10 times of events, the current item for inspection "LV" to the next item for inspection "PW" is 6 times, that the current item for inspection "LV" to the next item for inspection "CW" is 3 times, and that the current item for inspection "LV" to the next item for inspection "END" is 1 time. Supposed that, this time, the eleventh event arises as the current item for inspection "LV" to the next item for inspection "PW", multiplication of the above-mentioned conditional probability being 0.54 makes updates of the implementation probability of the current item for inspection "LV" to the next item for inspection "PW" being 0.64×0.54, the implementation probability of the current item for inspection "LV" to the next item for inspection "CW" being 0.27×0.54, and the implementation probability of the current item for inspection "LV" to the next item for inspection "END" being 0.09×0.54, respectively. Moreover, the conditional probability for transfer of "second time item for inspection" to "third time item for inspection" is the implementation probability of the current item for inspection "LV" to the next item for inspection "PW" being 0.64×0.54.

Upon change of the implementation frequency in the current item for inspection "LV" to the next item for inspection "PW", the controlling section 7 recalculates the implementation probabilities of the current item for inspection "LV" to the next item for inspection "PW", the current item for inspection "LV" to the next item for inspection "CW", and the current item for inspection "LV" to the next item for inspection "END", respectively, and stores the individual calculated implementation probabilities in the combining and storing section 5d.

[Step S107: PW]

The controlling section 7 replaces the next item for inspection "PW" for the current item for inspection, and moves to step S103.

[Step S103: PW]

The controlling section 7 gives, to the ultrasonic wave transmitting and receiving section 4, the ultrasonogram forming section 5 and the displaying section 6, control amounts for measuring the current item for measurement "PW" which is performed upon accepting the input from the inputting device.

Figure 9:
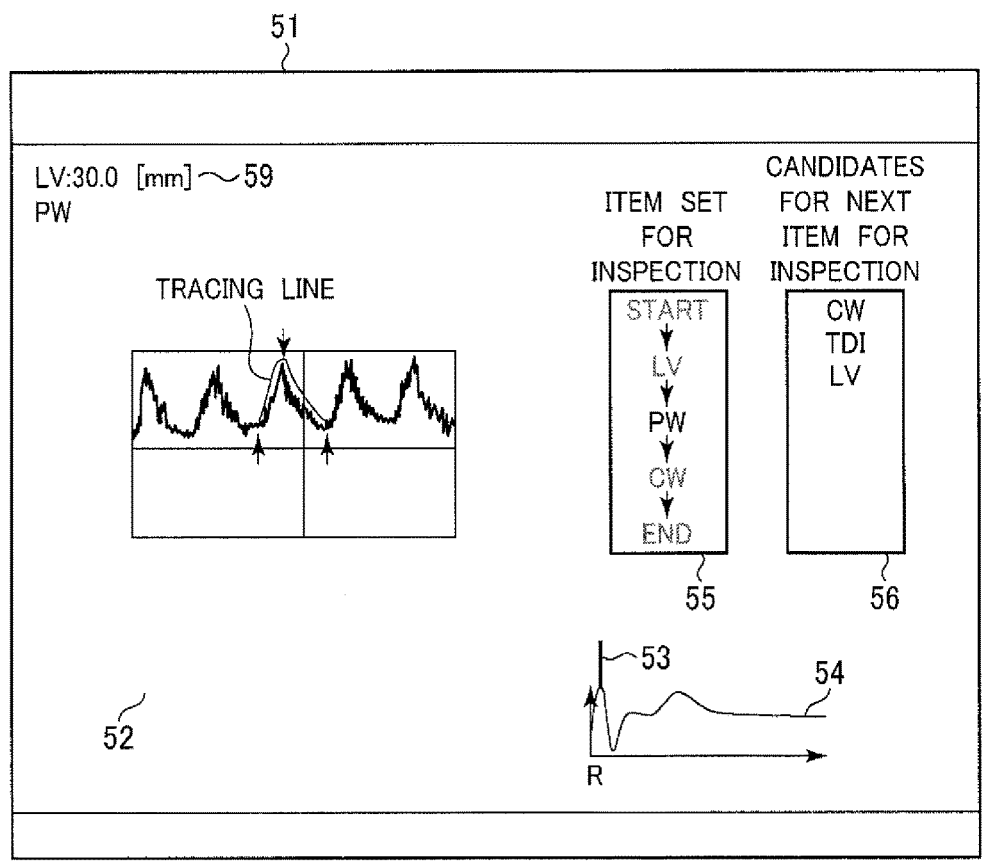
FIG. 9 is a diagram for explaining a display example of the displaying section 6 in "second time item for inspection" which is one process of operation in FIG. 6.

Thereby, the displayed state of the displaying section 6 is moved from FIG. 8 to FIG. 9.

FIG. 9 is a diagram for explaining a display example of the displaying section 6 in "second time item for inspection" which is a process of operation in FIG. 6. As to the individual signs in FIG. 9, the portion which is described in FIG. 5 is omitted and a different portion from FIG. 5 is described. In the displaying region 55 of the item set for inspection is FIG. 9, the current item for inspection PW is in the displayed state and the items for inspection except the current item for inspection PW are in the non-displayed state in which they are indicated by outlined characters, and thereby, the current item for inspection can be discriminated from the other items for inspection, these being displayed.

Since the description of the operation of the ultrasonic probe 3 and the ultrasonic wave transmitting and receiving section 4 is same as the content described in step S103: LV, the description for these is omitted. The ultrasonogram forming section 5 forms a Doppler spectrum due to pulse Doppler from the electric signal having undergone the signal processing. The displaying section 6 displays the Doppler spectrum due to pulse Doppler formed by the ultrasonogram forming section 5 in the displaying region 52.

As above, the implementation of the current item for measurement "PW" completes.

[Step S104: PW to CW]

Although the inspector can perform selection and input arbitrary from the displayed candidates for the next item for inspection at this stage, the selection and input is not supposed to be performed in this case.

The controlling section 7 determines the presence or absence of a next item for inspection in the item set for inspection. In this case, since the next item for inspection "CW" of the current item for inspection "PW" is present, the controlling section 7 performs branching to the presence of a next item for inspection, that is, "y" and moves to step S105.

[Step S105: CW]

The controlling section 7 reads out the next item for inspection "CW" from the combining and storing section 5d, and displays it in the displaying region 56.

[Step S106: CW]

Since the implementation frequency in the current item for inspection "PW" to the next item for inspection "CW" increases by one event, the implementation probability of the current item for inspection "PW" to the next item for inspection "CW" is to be updated similarly to step S106: LV.

Since the implementation frequency in the current item for inspection "PW" to the next item for inspection "CW" increases by one event, the controlling section 7 updates the implementation probability of the current item for inspection "PW" to the next item for inspection "CW".

For example, as shown in FIG. 4, the implementation probability of the current item for inspection "PW" to the next item for inspection "CW" is 0.9, the implementation probability of the current item for inspection "PW" to the next item for inspection "LV" is 0.1, and the implementation probability of the current item for inspection "PW" to the next item for inspection "END" is 0.3. It is supposed that the basis of these probability calculations is in that, out of 10 times of events, the current item for inspection "PW" to the next item for inspection "CW" is 9 times, that the current item for inspection "PW" to the next item for inspection "LV" is 1 time, and that the current item for inspection "PW" to the next item for inspection "END" is 3 times. Supposed that, this time, the eleventh event arises as the current item for inspection "PW" to the next item for inspection "CW", multiplication of the above-mentioned conditional probability being 0.64×0.54 makes updates of the implementation probability of the current item for inspection "PW" to the next item for inspection "CW" being 0.81×0.64×0.54, the implementation probability of the current item for inspection "PW" to the next item for inspection "LV" being 0.09×0.64×0.54, and the implementation probability of the current item for inspection "PW" to the next item for inspection "END" being 0.27×0.64×0.54, respectively.

Upon change of the implementation frequency in the current item for inspection "PW" to the next item for inspection "CW", the controlling section 7 recalculates the implementation probabilities of the current item for inspection "PW" to the next item for inspection "CW", the current item for inspection "PW" to the next item for inspection "LV", and the current item for inspection "PW" to the next item for inspection "END", respectively, and stores the individual implementation probabilities in the combining and storing section 5d.

[Step S107: CW]

The controlling section 7 replaces the next item for inspection "CW" for the current item for inspection, and moves to step S103.

[Step S103: CW]

The controlling section 7 gives, to the ultrasonic wave transmitting and receiving section 4, the ultrasonogram forming section 5 and the displaying section 6, control amounts for measuring the current item for measurement "CW" which is performed upon accepting the input from the inputting device.

Figure 10:
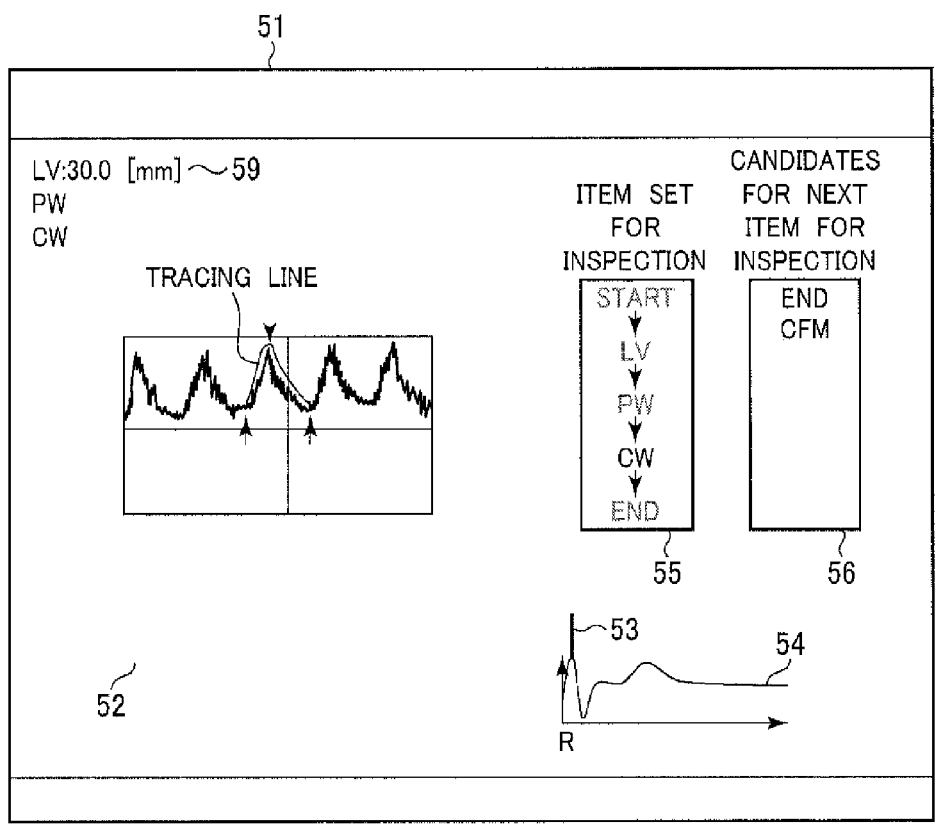
FIG. 10 is a diagram for explaining a display example of the displaying section 6 in "third time item for inspection" which is one process on operation in FIG. 6.

Thereby, the displayed state of the displaying section 6 is moved from FIG. 9 to FIG. 10.

FIG. 10 is a diagram for explaining as a display example of the displaying section 6 in "third time item for inspection" which is a process of operation in FIG. 6. As to the individual signs in FIG. 10, the portion which is described in FIG. 5 is omitted and a different portion from FIG. 5 is described. In the displaying region 55 of the item set for inspection in FIG. 10, the current item for inspection CW is in the displayed state and the items for inspection except the current item for inspection CW are in the non-displayed state in which they are indicated by outlined characters, and thereby, the current item for inspection can be discriminated from the other items for inspection, these being displayed.

Since the description of the operation of the ultrasonic probe 3 and the ultrasonic wave transmitting and receiving section 4 is same as the content described in step S103: LV, the description for these is omitted. The ultrasonogram forming section 5 forms a Doppler spectrum due to continuous wave Doppler from the electric signal having undergone the signal processing. The displaying section 6 displays the Doppler spectrum due to continuous wave Doppler formed by the ultrasonogram forming section 5 in the displaying region 52. The merit of "PW" is that it has distance resolution. Instead, the restricting conditions of the maximum detection frequency and the maximum detection depth arise, not arising for "CW". On the other hand, the feature of "CW" is no practical measurement limit in high-speed blood flow measurement. However, "CW" does not have positional resolution and the position of the generation source of a received signal cannot be known. Therefore, both of "PW" and "CW" are performed in order to complement the demerits of both of "PW" and "CW".

As above, the implementation of the current item for measurement "CW" completes.

[Step S104: CW to END]

The controlling section 7 determines the presence or absence of a next item for inspection. In this case, since a next item for inspection "END" of the current item for inspection "CW" is not present, the controlling section 7 performs branching to the absence of a next item for inspection, that is, "n" and moves to step S108. An example of movement to step S108 is shown in FIG. 11 as a display example.

Whereas, "END" may be displayed in the displaying region 56 in order to clarify the end of the processing.

Figure 11:
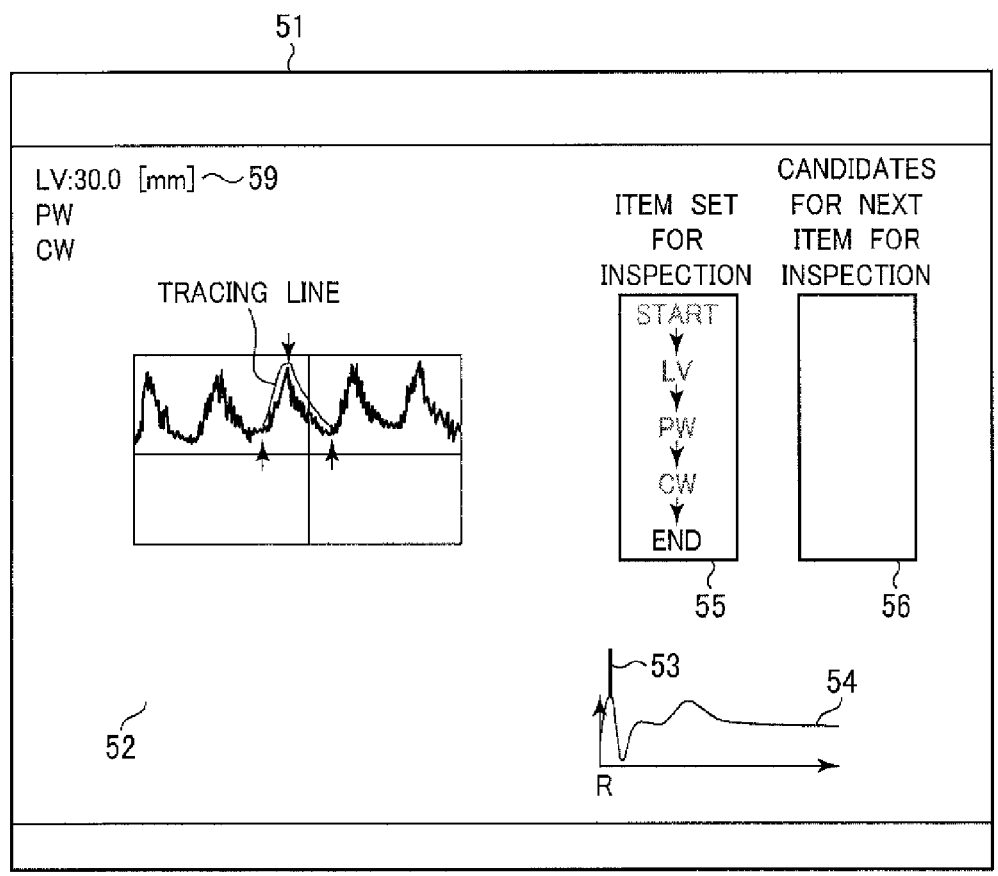
FIG. 11 is a diagram for explaining a display example of the displaying section 6 in "inspection end (END)" which is one process on operation in FIG. 6.

FIG. 11 is a diagram for explaining a display example of the displaying section 6 in "inspection end (END)" which is a process of operation in FIG. 6.

[Step S108]

The inspector inputs whether or not the position of the ultrasonic probe 3 is reconfigured to continue another item set for measurement or the like using the inputting section 8.

Upon accepting the input of the inputting section 8, the controlling section 7 moves to step S102 when another item set for measurement or the like is continued or moves to step S109 when reconfiguration is not performed.

[Step S109]

The inspector inputs whether or not the measurement is ended using the inputting section 8.

Upon accepting the input of the inputting section 8, the controlling section 7 moves to END when the measurement is ended or moves to step S101 when the measurement is not ended.

According to Embodiment 1 described above, since a plurality of items for inspection including ultrasonic imaging or measurement of an imaged ultrasonogram and an order thereof are stored, regarding an item set for inspection constituted of a next item for inspection which is an item for inspection subsequent to a current item for inspection currently being implemented out of the plurality of items for inspection, an implementation frequency at which the item set for inspection is implemented, for each next item for inspection is calculated, an implementation probability in which the item set for inspection is implemented is calculated by calculating a non-implementation frequency for each next item for inspection for which the item set for inspection has not been sequentially implemented and an overall frequency obtained by adding the implementation frequency and the non-implementation frequency and by dividing the implementation frequency by the overall frequency, a candidate for the next item for inspection on the basis of the implementation frequency is displayed, and the next item for inspection from the candidate for the next item for inspection is inputted, operability in selecting a plurality of items for inspection subsequent after the current item for inspection in an item set for inspection can be improved.

Moreover, due to the particular effect of Embodiment 1, candidates for an item for inspection next to an item for inspection currently being implemented in an item set for inspection can be presented to the inspector. Furthermore, since inspection to be performed according to time phase can be presented by synchronizing it with time phase of a biological signal such as the electrocardiogram 54, a next item for inspection more suitable for an inspection circumstance can be presented.

Embodiment 2

Embodiment 2 is described using figures. In Embodiment 2, a different point from Embodiment 1 is in the case of using a decision tree in FIG. 12 in place of the Markov model in FIG. 4.

Since the configuration of the ultrasonic diagnosis apparatus is described in Embodiment 1 using FIG. 1, its description is omitted in Embodiment 2. In the configuration of the ultrasonogram forming section 5 in the ultrasonic diagnosis apparatus, while one stored in the combining and storing section 5d in Embodiment 1 is the Markov model shown in FIG. 4, that in Embodiment 2 is the decision tree shown in FIG. 12, this being the difference. Except the above-mentioned difference, the description of the configuration of the ultrasonogram forming section 5 is omitted in Embodiment 2. Moreover, as to the combining and storing section 5d described in FIG. 3 for Embodiment 1, since the database of item sets for inspection is also same as in Embodiment 2, its description in Embodiment 2 is omitted. Moreover, a method of the presentation may employ, for example, a descending order of frequency.

Figure 12:
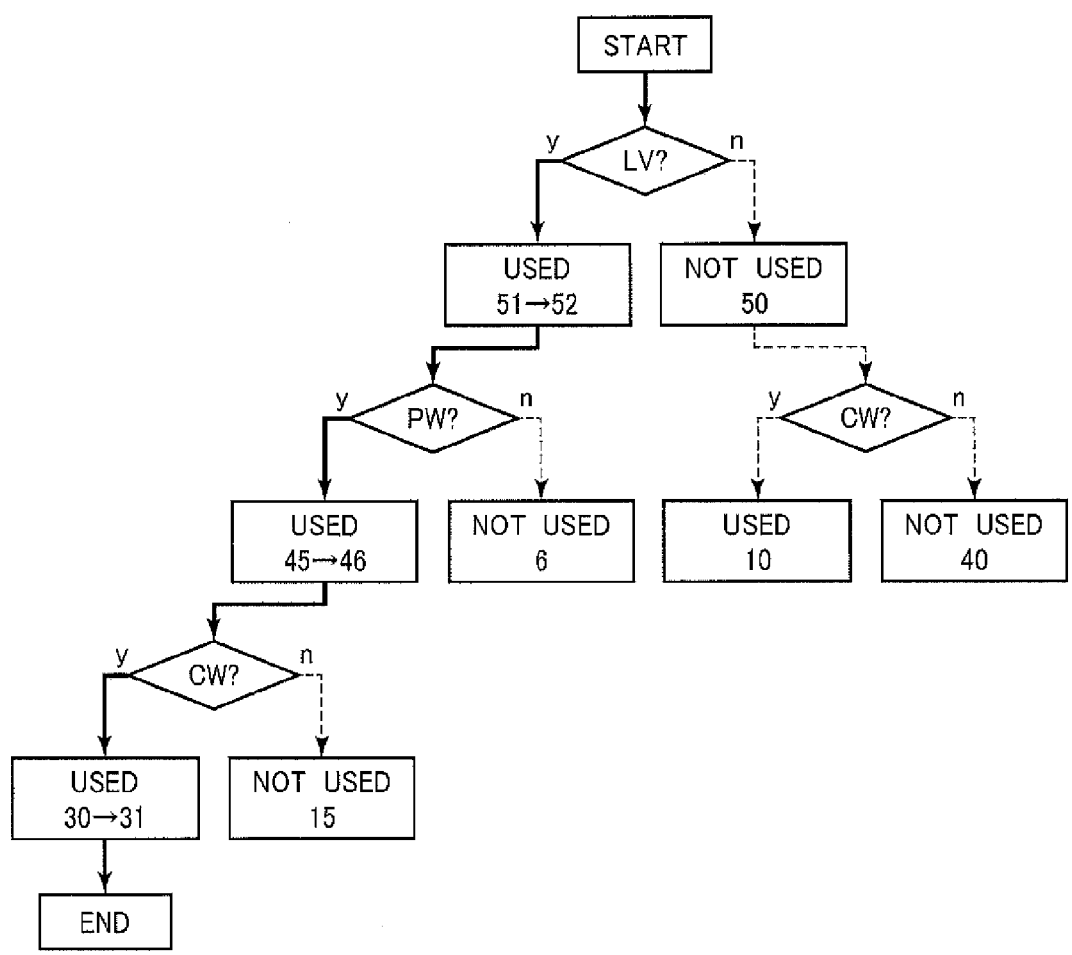
FIG. 12 is a diagram for explaining a calculation function of implementation probabilities of items for inspection using a decision tree according to Embodiment 2.

FIG. 12 is a diagram for explaining a calculation function of implementation frequencies of items for inspection using the decision tree according to Embodiment 2.

The controlling section 7 has a calculation function of implementation frequencies of items for inspection by which an implementation frequency of a next item for inspection with respect to a current item for inspection is calculated for each item for inspection in an item set for inspection for the past item sets for inspection stored in the database of item sets for inspection in the combining and storing section 5d.

The calculation function of implementation frequencies of items for inspection shown in FIG. 12 is described using an example of transition of "inspection start" to "LV" to "PW" to "CW" to "inspection end" in "heart inspection 2".

First, in "inspection start", a frequency of using "LV" being 51 and a frequency of not using being 50 are stored for a next item for inspection (first time item for inspection) in the combining and storing section 5d, respectively. Herein, as indicated by a bold arrow in the figure, using "LV" for "first time item for inspection" is selected. Due to this selection, the frequency of using "LV" for "first time item for inspection" increases to 52.

Next, in "first time item for inspection", for the next item for inspection (second time item for inspection), a frequency of using "PW" being 45 and a frequency of not using "PW" being 6 are stored in the combining and storing section 5d, respectively. Herein, as indicated by a bold arrow in the figure, using "PW" for "second time item for inspection" is selected. Due to this selection, the frequency of using "PW" for "second time item for inspection" increases to 46.

Next, in "second time item for inspection", for the next item for inspection (third time item for inspection), a frequency of using "CW" being 30 and a frequency of not using "CW" being 15 are stored in the combining and storing section 5d, respectively. Herein, as indicated by a bold arrow in the figure, using "CW" for "third time item for inspection" is selected. Due to this selection, the frequency of using "CW" for "third time item for inspection" increases to 31.

Finally, in "third time item for inspection", for the next item for inspection (inspection end), as indicated by a bold arrow in the figure, "inspection end" is selected.

The controlling section 7 causes the combining and storing section 5d to store the implementation frequencies of the individual calculated next items for inspection.

Moreover, since the display of the next item for inspection is same as that described in Embodiment 1 using FIG. 5, the description in Embodiment 2 is omitted.

Figure 13:
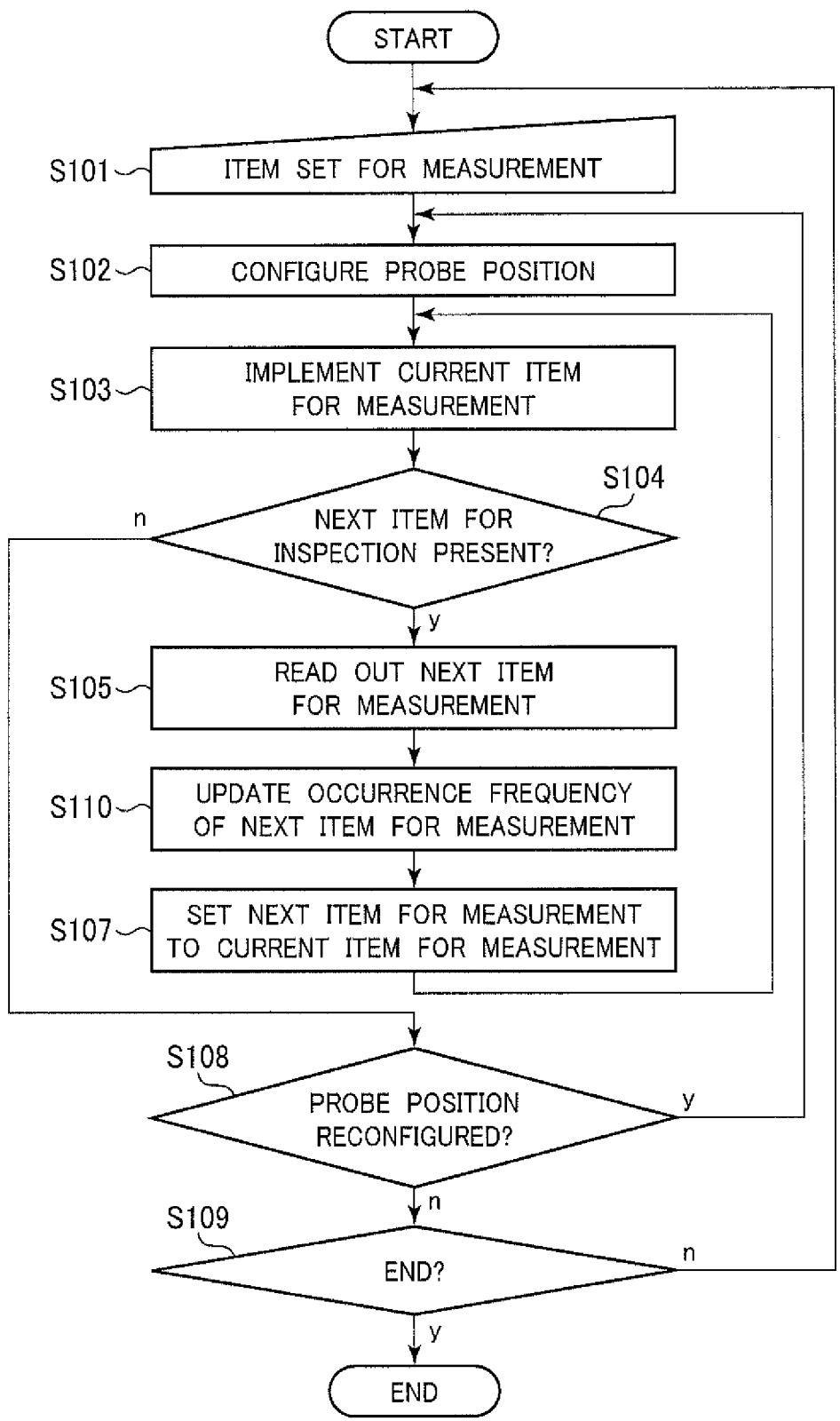
FIG. 13 is a flowchart for explaining an operation example according to Embodiment 2.

Moreover, an operation example according to Embodiment 2 is described using FIG. 13. FIG. 13 is a flowchart for explaining an operation example according to Embodiment 2.

It is noted that, except the following difference, the description in Embodiment 1 using FIG. 6 to FIG. 11 applies as being same, and therefore, the description is omitted in Embodiment 2.

While the implementation probability is calculated in Embodiment 1, the item for inspection in step S106 being an event, the implementation frequency is calculated in Embodiment 2, the item for inspection in step S110 being an event.

[Step S110: PW]

The implementation frequency in the current item for inspection "LV" to the next item for inspection "PW" is to be updated since the implementation frequency in the current item for inspection "LV" to the next item for inspection "PW" increases by one event.

Upon change of the implementation frequency in the current item for inspection "LV" to the next item for inspection "PW", the controlling section 7 recalculates the implementation frequencies in the current item for inspection "LV" to the next item for inspection "PW", the current item for inspection "LV" to the next item for inspection "CW", and the current item for inspection "LV" to the next item for inspection "END", respectively, and stores the individual calculated implementation frequencies in the combining and storing section 5d.

[Step S110: CW]

The implementation frequency in the current item for inspection "PW" to the next item for inspection "CW" is to be updated similarly to step S106: LV since the implementation frequency in the current item for inspection "PW" to the next item for inspection "CW" increases by one event.

Upon change of the implementation frequency in the current item for inspection "PW" to the next item for inspection "CW", the controlling section 7 recalculates the implementation frequencies in the current item for inspection "PW" to the next item for inspection "CW", the current item for inspection "PW" to the next item for inspection "LV", and the current item for inspection "PW" to the next item for inspection "END", respectively, and stores the individual calculated implementation frequencies in the combining and storing section 5d.

According to Embodiment 2 described above, by including a storing section storing a plurality of items for inspection including ultrasonic imaging or measurement of an imaged ultrasonogram and an order thereof, a controlling section calculating, regarding an item set for inspection constituted of a next item for inspection which is an item for inspection subsequent to a current item for inspection which is currently being implemented out of the plurality of items for inspection, an implementation frequency at which the item set for inspection is implemented, for each next item for inspection, a displaying section displaying a candidate for the next item for inspection on the basis of the implementation frequency, and an inputting section inputting the next item for inspection out of the candidate for the next item for inspection, operability in selecting a plurality of items for inspection subsequent after the current item for inspection in an item set for inspection can be improved.

Moreover, due to the particular effect of Embodiment 2, compared with the calculation of implementation probabilities in Embodiment 1, only the calculation of implementation frequencies is required, and therefore, any circuit or program for point operations is not required and the circuit configuration and programming can be simplified.

Embodiment 3

Embodiment 3 is described using figures. In Embodiment 3, a different point from Embodiment 1 is in the case of changing in the midway of an item set for measurement for the Markov model in FIG. 4, as shown in FIG. 14.

Since the configuration of the ultrasonic diagnosis apparatus is described in Embodiment 1 using FIG. 1 and FIG. 2, its description is omitted in Embodiment 2.

Figure 14:
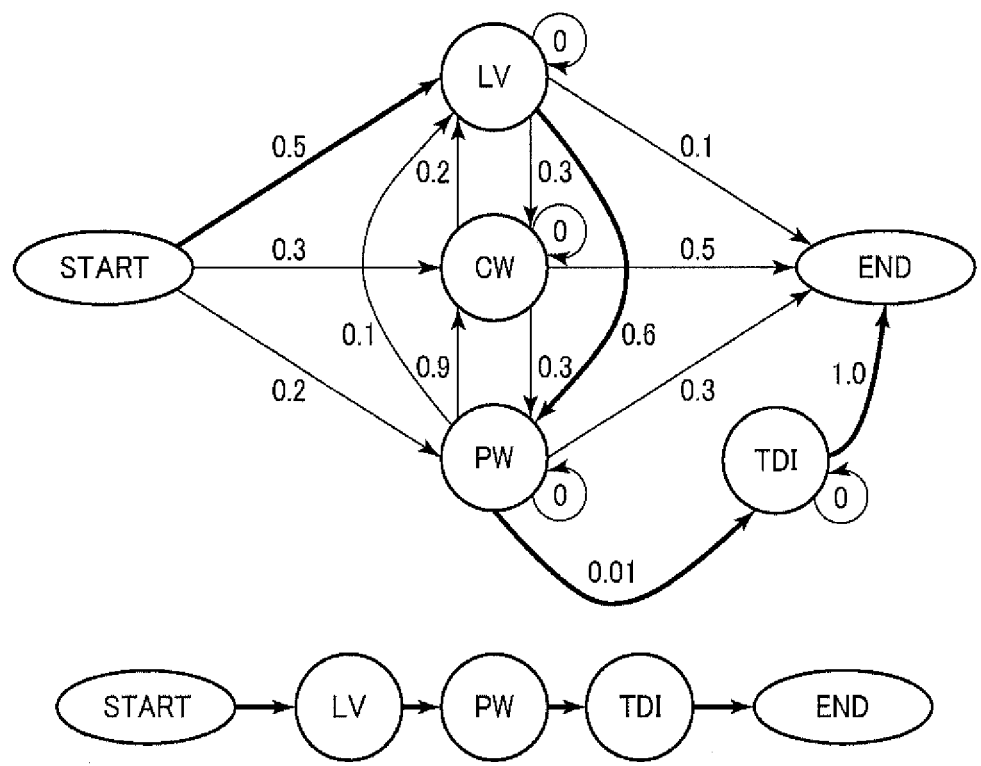
FIG. 14 is a diagram for explaining a calculation function of implementation probabilities of items for inspection using a Markov model according to Embodiment 3.

FIG. 14 is a diagram for explaining a calculation function of implementation probabilities of items for inspection using a Markov model according to Embodiment 3.

As to a calculation function of implementation frequencies of items for inspection shown in FIG. 14, only the different portion from Embodiment 1 is described using an example of transition of "TDI" to "inspection end" in place of "inspection start" to "LV" to "PW" to "CW" in "heart inspection 2".

Next, in "second time item for inspection", for the next item for inspection (third time item for inspection), the implementation probability of "LV" being 0.1, the implementation probability of "PW" being 0 and the implementation probability of "CW" being 0.9 are stored along with the past item sets for inspection in the combining and storing section 5d. Herein, as indicated by a bold arrow in the figure, "TDI" is newly selected as "third time item for inspection". An implementation probability of 0.01 is given to "TDI" thus selected.

The controlling section 7 causes the combining and storing section 5d to store the implementation probabilities of the individual calculated next items for inspection.

Moreover, since the display of the next item for inspection is same as that described in Embodiment 1 using FIG. 5, its description is omitted in Embodiment 2.

Figure 15:
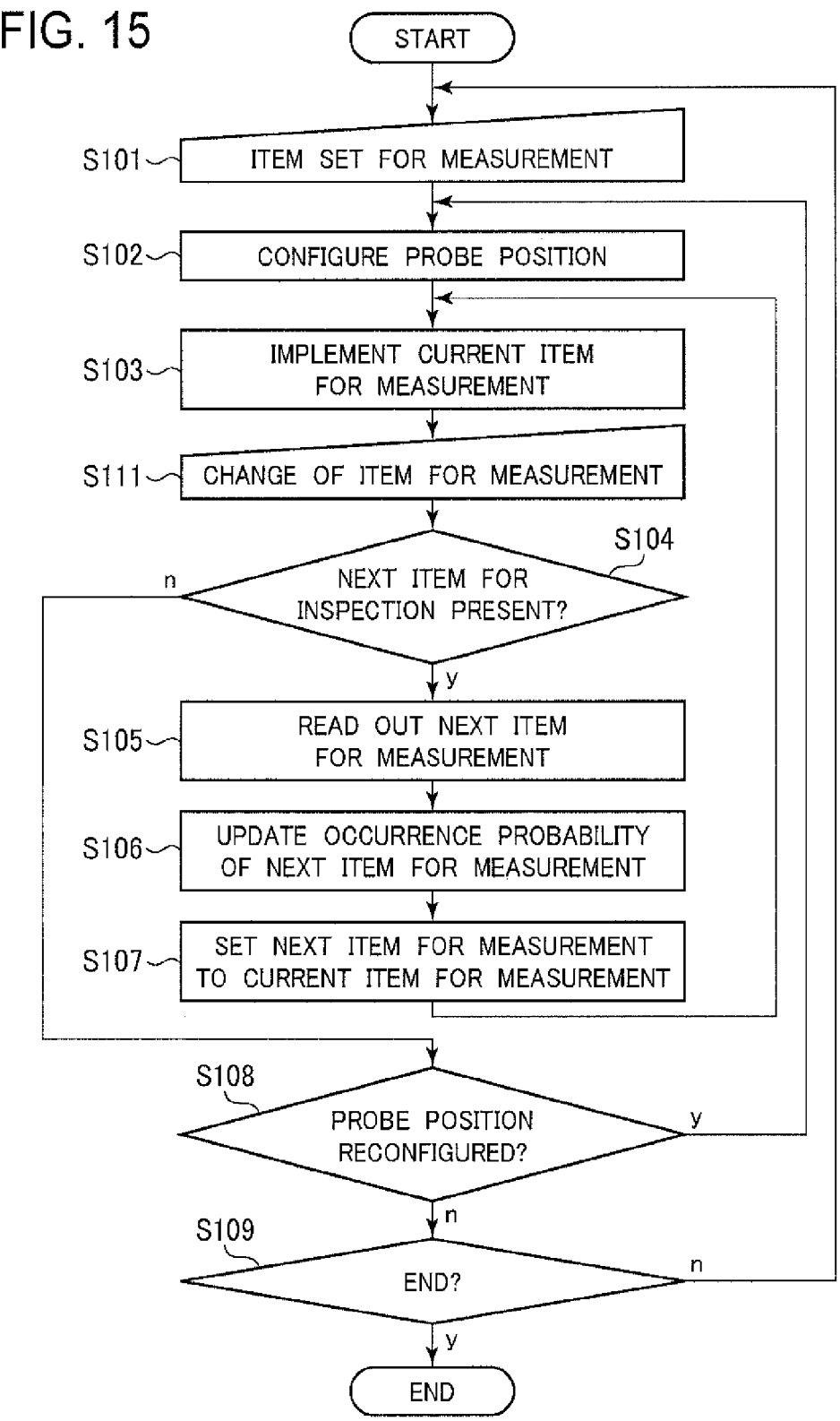
FIG. 15 is a flowchart for explaining an operation example according to Embodiment 3.

Moreover, an operation example according to Embodiment 3 is described using FIG. 15. FIG. 15 is a flowchart for explaining an operation example according to Embodiment 3.

It is noted that, except the following difference, the description in Embodiment 1 using FIG. 6 to FIG. 11 applies as being same, and therefore, the description is omitted in Embodiment 3.

In Embodiment 3, step S111 as follows is added between step S103 and step S104.

[Step S111]

The inspector inputs change of the item for measurement. Upon the input of change of the item for measurement, the controlling section 7 changes part of the items for measurement in the item set for measurement. Herein as illustrated in FIG. 16, "third time item for inspection" is changed from "CW" to "TDI".

Figure 16:
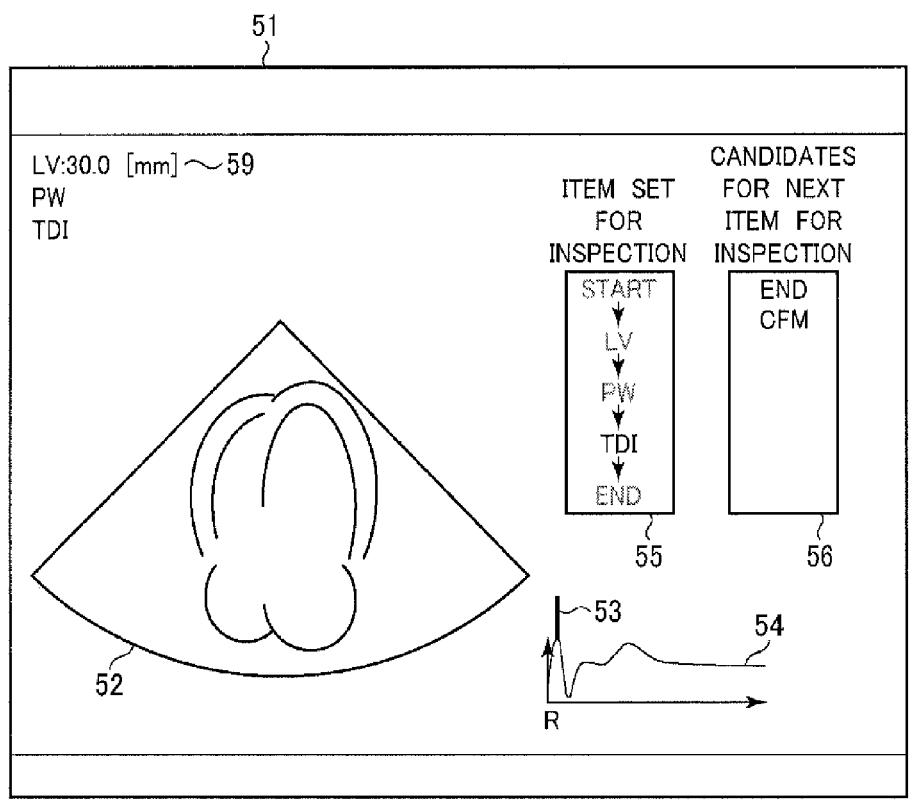
FIG. 16 is a diagram for explaining a display example of the displaying section 6 in "third time item for inspection" which is one process of operation in FIG. 15.

FIG. 16 is a diagram for explaining a display example of the displaying section 6 in "third time item for inspection" which is one process of operation in FIG. 15.

Upon the change of the implementation frequency of the current item for inspection "TDI", the controlling section 7 recalculates the implementation frequencies of the current item for inspection "LV" to the next item for inspection "PW", the current item for inspection "LV" to the next item for inspection "CW", and the current item for inspection "LV" to the next item for inspection "END", respectively, and stores individual calculated implementation probabilities in the combining and storing section 5d.

According to Embodiment 3 described above, similarly to Embodiment 1, operability in selecting a plurality of items for inspection subsequent after a current item for inspection in an item set for inspection can be improved. In other words, since part of the item set for measurement according to Embodiment 1 can be changed, flexibility of items for measurement can be improved, not fixing the only items for measurement.

Moreover, due to the particular effect of Embodiment 3, since the operations of the individual items for inspection can be confirmed in an item set for inspection, reliability of the operations of the individual items for inspection can be improved.

Moreover, Embodiment 3 is described using implementation probabilities of items for measurement, whereas it may be done using implementation frequencies of items for measurement described in Embodiment 2.

As above, the embodiments according to the present invention are described, whereas the present invention is not limited to these.

REFERENCE SIGNS LIST

1: ultrasonic diagnosis apparatus, 3: ultrasonic probe, 4: ultrasonic wave transmitting and receiving section, 5: ultrasonogram forming section, 5a: ultrasonogram information generating section, 5b: digital scan converter (DSC) section, 5c: graphic data generating section, 5d: combining and storing section, 5e: interface, 6: displaying section, 7: controlling section, 8: inputting section

The invention claimed is:

1. An ultrasonic diagnosis apparatus comprising:
an ultrasonic wave transmitting and receiving device, configured to transmit and receive a signal used to generate an ultrasonic signal transmitted and received by an ultrasonic probe, and configured to perform signal processing on a signal received by the ultrasonic probe;
an ultrasonogram forming device configured to generate a plurality of items for inspection using the signal received by the ultrasonic probe;
a memory configured to store a plurality of items for inspection including ultrasonic imaging or measurement of an imaged ultrasonogram and an order of the items;
a controller configured to calculate, regarding an item set for inspection constituted of a next item for inspection which is an item for inspection subsequent to a current item for inspection which is currently being implemented out of the plurality of items for inspection, an implementation frequency at which the item set for inspection is implemented, for each next item for inspection;
a display configured to display a candidate for the next item for inspection on the basis of the implementation frequency; and
an input device configured to input the next item for inspection from the candidate for the next item for inspection,
wherein:
if a number of total events is increased by one increment by once implementing an event in which the current item for inspection changes to the next item for inspection, then the controller calculates an implementation probability of the implemented event using a first implementation probability formula, and the implementation probability of an unimplemented event using a second implementation probability formula,
the input device newly inputs a next item for inspection, and
the controller newly calculates an item set for inspection constituted of the newly inputted next item for inspection and the current item for inspection,
wherein:
the first implementation probability formula represents: (a number of relevant events in the past+1)/(a number of total events in the past+1), and
the second implementation probability formula represents: the number of relevant events in the past/(the number of total events in the past+1).

2. The ultrasonic diagnosis apparatus according to claim 1, wherein
the display displays the current item for inspection and the next item for inspection in different displaying modes.

3. The ultrasonic diagnosis apparatus according to claim 1, wherein
the display displays the implementation probability in a displaying region different from a displaying region of the ultrasonogram.

4. The ultrasonic diagnosis apparatus according to claim 1, wherein
the controller calculates a conditional probability of a second item for inspection which is an item for inspection next to the next item for inspection on the basis of implementation probabilities of the next item for inspection and the current item for inspection.

5. A method for presenting items for inspection in an ultrasonic diagnosis apparatus, the method comprising:
receiving reflected echo signals from an object;
performing signal processing on the reflected echo signals;
generating a plurality of items for inspection using the reflected echo signals;
a first step of storing the plurality of items for inspection including ultrasonic imaging or measurement of an imaged ultrasonogram and an order of the items;
a second step of using a controller to calculate, regarding an item set for inspection constituted of a next item for inspection which is an item for inspection subsequent to a current item for inspection which is currently being implemented out of the plurality of items for inspection, an implementation frequency at which the item set for inspection is implemented, for each next item for inspection;

a third step of displaying a candidate for the next item for inspection on the basis of the implementation frequency;

a fourth step of inputting the next item for inspection from the candidate for the next item for inspection, calculating an implementation probability of an implemented event using a first implementation probability formula, and the implementation probability of an unimplemented event using a second implementation probability formula if a number of total events is increased by one increment by once implementing the event in which the current item for inspection changes to the next item for inspection, a fifth step of newly inputting a next item for inspection, and using the controller to calculate an item set for inspection constituted of the newly inputted next item for inspection and the current item for inspection, wherein:
the first implementation probability formula represents: (a number of relevant events in the past+1)/(a number of total events in the past+1), and
the second implementation probability formula represents: the number of relevant events in the past/(the number of total events in the past+1).

6. The method for presenting items for inspection in an ultrasonic diagnosis apparatus according to claim 5, wherein
in the second step, an implementation probability in which the item set for inspection is implemented by calculating a non-implementation frequency for each next item for inspection for which the item set for inspection has not been sequentially implemented and an overall frequency obtained by adding the implementation frequency and the non-implementation frequency and by dividing the implementation frequency by the overall frequency is calculated, and
in the third step, the candidate of the next item for inspection on the basis of the implementation probability is displayed.

7. The method for presenting items for inspection in an ultrasonic diagnosis apparatus according to claim 6, wherein
in the third step, the candidate for the next item for inspection is displayed in descending order of probability on the basis of the implementation probability.

8. The method for presenting items for inspection in an ultrasonic diagnosis apparatus according to claim 5, wherein
in the third step, the current item for inspection and the next item for inspection are displayed in different displaying modes.

9. The method for presenting items for inspection in an ultrasonic diagnosis apparatus according to claim 5, wherein
in the third step, the implementation frequency is displayed in a displaying region different from a displaying region of the ultrasonogram.

10. The method for presenting items for inspection in an ultrasonic diagnosis apparatus according to claim 5, wherein
in the third step, the candidate for the next item for inspection is displayed in descending order of frequency on the basis of the implementation frequency.

11. The method for presenting items for inspection in an ultrasonic diagnosis apparatus according to claim 5, wherein
in the fourth step, a next item for inspection is newly inputted, and
in the third step, an item set for inspection constituted of the newly inputted next item for inspection and the current item for inspection is newly calculated.

\* \* \* \* \*